United States Patent [19]

Bharucha et al.

[11] 4,362,746

[45] Dec. 7, 1982

[54] ANTIVIRAL 1,2,3,4-TETRAHYDRO-1,4-METHANONAPH-THALENE DERIVATIVES

[75] Inventors: Kekhusroo R. Bharucha, Toronto; Kam C. Tin, Etobicoke; Iva Ajdukovic; Djordje Ajdukovic, both of Beaconsfield, all of Canada

[73] Assignees: Canada Packers Inc., Ontario; The Institute of Microbiology and Hygiene of the University of Montreal, Quebec, both of Canada

[21] Appl. No.: 226,640

[22] Filed: Jan. 21, 1981

[51] Int. Cl.$^3$ .................. A61K 31/135; C07C 87/453
[52] U.S. Cl. ..................................... 424/330; 564/387; 564/427; 549/37
[58] Field of Search ................. 564/387, 427; 424/330

[56] References Cited

U.S. PATENT DOCUMENTS 3,932,512  1/1976  Bharucha et al. .................. 564/387
4,046,811  9/1977  Bharucha et al. .............. 424/330 X Primary Examiner—Bernard Helfin
Attorney, Agent, or Firm—Bacon & Thomas

[57] ABSTRACT

Derivatives of 1,2,3,4-tetrahydro-1,4-methanonaphthalene, and the use of such compounds to control viral infections, particularly influenza virus, in warm-blooded animals are disclosed. Pharmaceutical compositions containing an antiviral effective amount of the novel compounds and a pharmaceutically acceptable carrier are also disclosed.

8 Claims, No Drawings

ANTIVIRAL 1,2,3,4-TETRAHYDRO-1,4-METHANONAPHTHALENE DERIVATIVES

BACKGROUND OF THE INVENTION

The present invention relates to two derivatives of 1,2,3,4-tetrahydro-1,4-methanonaphthalene and their pharmaceutically acceptable acid addition salts and to the production and use of said compounds as antiviral agents.

It is an object of the present invention to provide new antiviral agents, a process for preparing same and pharmaceutical compositions and methods of using them.

U.S. Pat. Nos. 3,932,512 and 4,046,811 disclose certain 1,2,3,4-tetrahydro-1,4-alkanonaphthalenes having antiviral activity. These patents also demonstrate the unpredictability of antiviral activity for any given compound. For example, the patents disclose that while the 1,2,3,4-tetrahydro-1,4-methanonaphthalen-endo-2-amine derivative exhibited antiviral activity, the isomer with the amino substituent taking up the exo configuration showed no antiviral activity. However, derivatives having both 2-endo amino and 3-exo substituents exhibited enhanced activity when compared to analogous compounds having different configurations.

SUMMARY OF THE INVENTION

It has now been discovered that certain other derivatives of 1,2,3,4-tetrahydro-1,4-methanonaphthalene exhibit antiviral activity. In particular, the compounds of the invention are characterized by low toxicity coupled with good activity against influenza virus, especially influenza virus $A_2$, as shown by standard tissue culture tests and by in vivo test in mice.

The new compounds of the invention are endo-2-dimethylaminomethyl-1,2,3,4-tetrahydro-1,4-methanonaphthalene and endo-3-dimethylaminomethyl-endo-2-amino-1,2,3,4-tetrahydro-1,4-methanonaphthalene. These compounds readily form acid addition salts and such salts having a non-toxic anion are also included within the scope of the invention. Representative of such salts are the hydrochloride, hydrobromide, sulfate, phosphate, acetate, succinate, adipate, propionate, tartrate, citrate, bicarbonate, pamoate, cyclohexylsulfamate and acetylsalicylate.

The compounds of the invention are useful for influenza viral prophylaxis as well as for therapeutic treatment. In general, it is preferred to administer them at a concentration level that will afford effective results without causing any harmful or deleterious side effect in the patient, i.e., in an effective non-toxic amount. The dosage administered to the patient will also be dependent upon the virus being treated, the age, health and weight of the recipient, the extent of infection, the kind of concurrent treatment if any, the frequency of treatment and the nature of the effect desired. For example, a daily dosage of 10 to 100 mg/kg of body weight of either compound of the invention dissolved or suspended in phosphate buffer solution (PBS) may be safely and effectively administered to mice by the intraperitoneal route. Dosages are readily adjusted by known procedures for administration to other animal hosts including human and avian hosts.

The compounds of the invention can be employed in dosage form in combination with pharmaceutically acceptable carriers, solvents, diluents and the like to provide liquid solutions or suspensions for intranasal or parenteral use.

In general, water, saline, aqueous dextrose (glucose) and related sugar solutions and glycols such as propylene glycol or polyethylene glycol are preferred liquid carriers, particularly for injectable solutions. Sterile injectable solutions such as buffered saline will ordinarily contain from about 0.5% to 25% by weight of the active ingredient.

DETAILED DESCRIPTION OF THE INVENTION

The general procedure for preparing the compounds of the invention is illustrated as follows:

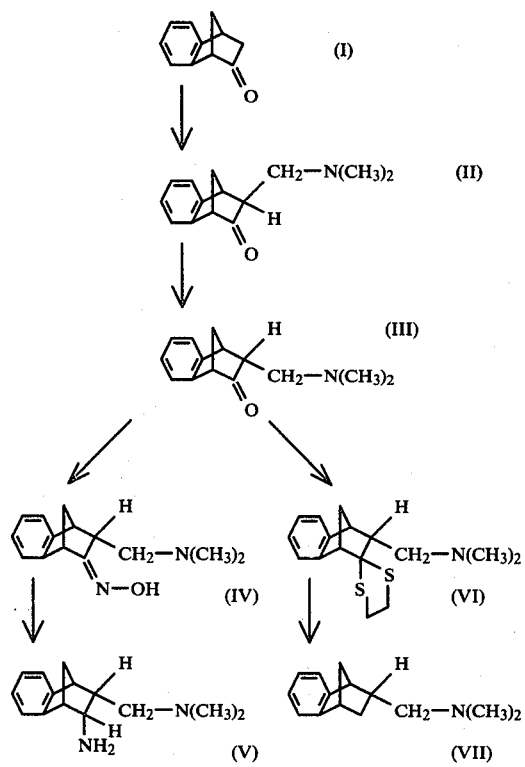

The starting material for the synthetic scheme outlined above is benzonorbornen-2-one, (I), which is prepared by the reaction of benzonorbornadiene (1,4-dihydro-1,4-methanonaphthalene) with formic acid, followed by oxidation of the exo-2-formate with a solution of chromic acid. The preferential exo attack by the formic acid on the benzonorbornadiene is well established in these types of compounds.

Mannich condensation of the benzonorbornen-2-one with paraformaldehyde and dimethylamine hydrochloride in dimethyl formamide at steam bath temperature produces exo-3-dimethylaminomethylbenzonorbornen-2-one, (II). To insure higher and more consistent yields it is preferred to conduct this reaction in an acidic medium obtained by bubbling in HCl gas for a few minutes prior to heating.

Epimerization to produce endo-3-dimethylaminomethylbenzonorbornen-2-one, (III), is achieved by refluxing the exo-isomer (II) in methanolic KOH solution in the presence of a small amount of water, e.g., 10%.

Endo-3-dimethylaminomethyl-endo-2-amino-1,2,3,4-tetrahydro-1,4-methanonaphthalene, (V), is prepared from the endo-substituted ketone (III) by reacting this compound with hydroxylamine hydrochloride in the presence of sodium acetate to form the corresponding oxime (IV). Reduction of the oxime with sodium metal in ethanol produces the endo-3-dimethylaminomethyl-endo-2-amino-1,2,3,4-tetrahydro-1,4-methanonaphthalene, (V), of the invention.

Endo-2-dimethylaminomethyl-1,2,3,4-tetrahydro-1,4-methanonaphthalene, (VII), is prepared from the endo-substituted ketone (III) by reacting this compound with ethanedithiol and boron trifluoride-etherate ($BF_3.Et_2O$) to produce the intermediate thioketal, (VI). The thioketal is reacted with Raney nickel in ethanol to produce the endo-2-dimethylaminomethyl-1,2,3,4-tetrahydro-1,4-methanonapthalene, (VII), of the invention.

To illustrate further the preparation of the compounds of the invention, the following examples are provided:

EXAMPLE 1

Preparation of endo-3-dimethylaminomethyl-endo-2-amino-1,2,3,4-tetrahydro-1,4-methanonaphthalene:

Benzonorbornen-2-one [Cook et al, *J. Org. Chem.*, 31, 14 (1966)] (200 g) was dissolved in 900 ml DMF together with 22 g paraformaldehyde and 125 g dimethylamine hydrochloride. HCl gas was bubbled through the reaction mixture for 1–2 minutes. The mixture was then heated at 100° C. (bath temp) for 20 hrs. On chilling a voluminous precipitate was produced (exo-3-dimethylaminomethylbenzonorbornen-2-one) which was filtered off, washed with cold $EtOH/Et_2O$ 2:1 and dried. The yield was 147.3 g, and a second crop of 24.2 g was obtained. 100 g exo-substituted ketone was dissolved in 475 ml MeOH. To this was added 1430 ml of a solution containing 381 g KOH and 143 ml water in MeOH. The reaction mixture was refluxed 21 hours, then allowed to stand at room temperature for 44 hours. The mixture was diluted with water and extracted with $CH_2Cl_2$ (3×750 ml). The organic layers were combined, dried over $MgSO_4$ and evaporated in vacuo to yield 77.2 g of free amine.

This material (endo-3-dimethylaminomethylbenzonorbornen-2-one) was combined with similar products from several other runs, converted to the hydrochloride and crystallized from $CH_2Cl_2$/pet. ether.

101 g of endo-substituted ketone, 35.5 g hydroxylammonium chloride and 81.8 g sodium acetate were dissolved in 1.0 l EtOH and 1.0 l $H_2O$. The solution was heated at reflux for 2.5 hours. The reaction mixture was then cooled, basified with satd.$Na_2CO_3$ solution and refrigerated. The resulting precipitate was filtered off, washed with water and dried in vacuo to yield 71.2 g of endo-3-dimethylaminomethylbenzonorbornen-2-oxime.

70.6 g oxime was dissolved in 4.5 l EtOH and heated to reflux. Heating was discontinued and 530 g sodium metal was added in small pieces at a rate sufficient to maintain reflux. After addition was complete, reflux was continued by external heating until all traces of sodium metal had dissolved. The reaction mixture was allowed to cool overnight, was diluted with an equal volume of water, and extracted in portions with $CH_2Cl_2$. The combined $CH_2Cl_2$ layers were dried over $MgSO_4$ and evaporated.

The crude diamine was dissolved in $CH_2Cl_2$, dry HCl gas was bubbled in and the solution was evaporated to dryness. The dihydrochloride was crystallized from $MeOH/Et_2O$. Two crops were obtained as shown.

A—30.11 g, m.p. 254° C. (decomp)

B—29.93 g, m.p. 255°–256° C. (decomp)

Crop B was recrystallized from $MeOH/Et_2O$ to yield C-23.53 g, m.p. 254° C. (decomp).

A and C were combined and crystallized from $MeOH/Et_2O$ 1:1 to yield 48.1 g of pure endo-3-dimethylaminomethyl-endo-2-amino-1,2,3,4-tetrahydro-1,4-methanonaphthalene dihydrochloride, m.p. 250°–252° C.

EXAMPLE 2

Preparation of endo-2-dimethylaminomethyl-1,2,3,4-tetrahydro-1,4-methanonaphthalene:

59.4 g of 3-endo-dimethylaminomethylbenzonorbornen-2-one (prepared as described in Example 1), 120 ml ethanedithiol and 120 ml $BF_3$-etherate were mixed and allowed to stand at room temperature for 18 hours. 45 ml MeOH and 910 ml $Et_2O$ were added and the mixture was refrigerated and then chilled further in a dry ice/acetone bath. The supernatant liquid was decanted from the resulting white solid. The solid was dispersed in satd. $Na_2CO_3$ solution (1.5 l) and extracted with $CHCl_3$ (4×1 l). The combined organic layers were dried over $MgSO_4$ and evaporated in vacuo to leave a pale yellow oil, 65.5 g.

10 g of thioketal was mixed with 60 ml Raney nickel in EtOH and an additional 300 ml abs EtOH was added. The mixture was refluxed for 6 hours and examined by TLC which showed that reaction was not complete. An additional 55 ml Raney nickel in EtOH plus 50 ml abs EtOH were added and reflux continued for a further 5 hours, at which time the TLC showed a single spot. The Raney nickel was filtered off through Celite, and the solution evaporated to dryness. The residue was taken up in $CH_2Cl_2/EtOH$, dry HCl gas was bubbled in, the solution was diluted with $Et_2O$ and allowed to crystallize at 5° C. The resulting crystals were filtered off, washed and dried, to yield 3.61 g endo-2-dimethylaminomethyl-1,2,3,4-tetrahydro-1,4-methanonaphthalene hydrochloride, mp. 187°–189° C.

ANTIVIRAL ACTIVITY

In Vitro Activity of Anti-Myxovirus Compounds

In preparing the compounds for testing, they were handled aseptically throughout. The compounds were dissolved in a minimum amount of a suitable solvent and the final dilutions were made up to the required volume in a complete culture medium used in assay and in concentration not exceeding the predetermined maximum non-toxic levels. Generally, all materials were tested first at three concentrations, and those which showed an inhibiting activity in that range were carefully retested at several concentrations below the maximum non-toxic levels.

The antiviral assays were done in tissue cultures infected with an appropriate dose of an influenza virus.

The cell culture used in all in vitro anti-myxovirus assays was an established cell line of the human conjunctiva (G-2 cells). The cytotoxic studies of each of the compounds were performed prior to testing for antiviral activity to determine level of response of the cells to the potentially toxic action of the compounds. Cytotoxic levels were expressed as concentration which produces 50% inhibition of the cell growth ($CTD_{50}$) as compared to the appropriate controls, or as a maximal non-toxic concentration which does not produce any morphologically detectable inhibition of the cell growth ($CTD_0$).

The viruses employed were $A_2$/Montreal/68, A/-Swine/1976/31 and $A_2$/Aichi/2/68. Standard batches of virus were made by growing the virus in an appropriate cell culture, after passaging it on the chick embryo, and then making a pool which was dispersed in ampoules and kept frozen at $-76°$ C. until used. The virus titer ($TCID_{50}$) was determined in the cell culture employed for the assays.

For the antiviral assays the cells were grown in triplicates per dilution of compound in test tubes in a suitable medium. Immediately before use the initial medium was replaced with the one containing the test compound in an appropriate concentration. After virus was added at approximately 10 and 100 $TCID_{50}$ dose levels the infected culture was incubated at 32° C. for a number of days. The medium was then drained, red blood cells added and after washing, the extent of hemadsorption evaluated. The percentage of inhibition of adsorption (a measure of antiviral activity) was then calculated. In all anti-myxovirus testing in vitro, as well as in vivo, amantadine (a known antiviral agent) was used as a reference standard.

The results of in vitro tests compared to amantadine are shown in the following table:

AMANTADINE HYDROCHLORIDE

Influenza $A_2$/MTL/68, G-2 Cells

| Cytotoxicity (ug/ml) | | Concentration of Compounds | % Inhibition |
|---|---|---|---|
| $CTD_{50}$ | $CTD_0$ | (ug/ml) | 316 $TCID_{50}$ |
| >100 | 100 | 100 | 54 |
| | | 90 | 46 |
| | | 80 | 42 |
| | | 70 | 16 |
| | | 60 | 0 |
| | | 50 | 0 |

Influenza $A_2$/Aichi/2/68, G-2 Cells

| Cytotoxicity (ug/ml) | | Concentration of Compounds | % Inhibition | |
|---|---|---|---|---|
| $CTD_{50}$ | $CTD_0$ | (ug/ml) | 100 $TCID_{50}$ | 52 $TCID_{50}$ |
| >100 | 100 | 100 | 43 | 87 |
| | | 90 | 67 | 97 |
| | | 80 | 27 | 70 |
| | | 70 | 33 | 83 |
| | | 60 | 0 | 53 |
| | | 50 | 0 | 0 |

Influenza A/Swine/1976/31, G-2 Cells

| Cytotoxicity (ug/ml) | | Concentration of Compounds | % Inhibition | |
|---|---|---|---|---|
| $CTD_{50}$ | $CTD_0$ | (ug/ml) | 316 $TCID_{50}$ | 178 $TCID_{50}$ |
| >100 | 100 | 100 | 100 | 100 |
| | | 90 | 100 | 100 |
| | | 80 | 100 | 100 |
| | | 70 | 97 | 93 |
| | | 60 | 83 | 90 |
| | | 50 | 67 | 80 |
| | | 40 | 10 | 17 |
| | | 30 | 0 | 0 |

ENDO-2-DIMETHYLAMINOMETHYL-1,2,3,4-TETRAHYDRO-1,4-METHANONAPHTHALENE HYDROCHLORIDE (COMPOUND A)

Influenza A/Swine/1976/31, G-2 Cells

| Cytotoxicity (ug/ml) | | Concentration of Compounds | % Inhibition | |
|---|---|---|---|---|
| $CTD_{50}$ | $CTD_0$ | (ug/ml) | 562 $TCID_{50}$ | 56 $TCID_{50}$ |
| 100 | 75 | 75 | 73 | 100 |
| | | 50 | 72 | 97 |
| | | 33 | 37 | 82 |
| | | 25 | 0 | 85 |
| | | 10 | 0 | 37 |
| | | 5 | 0 | 0 |

Influenza $A_2$/Mtl/68, G-2 Cells

| Cytotoxicity (ug/ml) | | Concentration of Compounds | % Inhibition | |
|---|---|---|---|---|
| $CTD_{50}$ | $CTD_0$ | (ug/ml) | 316 $TCID_{50}$ | 32 $TCID_{50}$ |
| 100 | 50 | 50 | 53 | 97 |
| | | 33 | 52 | 78 |
| | | 25 | 27 | 76 |
| | | 10 | 0 | 23 |
| | | 5 | 0 | 0 |

ENDO-3-DIMETHYLAMINOMETHYL-2-ENDO-AMINO-1,2,3,4-TETRAHYDRO-1,4-NAPHTHALENE DIHYDROCHLORIDE (Compound B)

Influenza $A_2$/MTL/68, G-2 Cells

| Cytotoxicity (ug/ml) | | Concentration of Compounds | % Inhibition | |
|---|---|---|---|---|
| $CTD_{50}$ | $CTD_0$ | (ug/ml) | 316 $TCID_{50}$ | 32 $TCID_{50}$ |
| 100 | 50 | 50 | 83 | 93 |
| | | 33 | 76 | 93 |
| | | 25 | 70 | 78 |
| | | 10 | 0 | 30 |
| | | 5 | 0 | 0 |

Influenza A/Swine/1976/31, G-2 Cells

| Cytotoxicity (ug/ml) | | Concentration of Compounds | % Inhibition |
|---|---|---|---|
| $CTD_{50}$ | $CTD_0$ | (ug/ml) | 316 $TCID_{50}$ |
| 100 | 50 | 33 | 100 |
| | | 25 | 92 |
| | | 10 | 70 |
| | | 5 | 0 |

Influenza B/MASS/66, G-2 Cells

| Cytotoxicity (ug/ml) | | Concentration of Compounds | % Inhibition |
|---|---|---|---|
| $CTD_{50}$ | $CTD_0$ | (ug/ml) | 56 $TCID_{50}$ |
| >100 | 50 | 50 | 73 |
| | | 33 | 43 |
| | | 25 | 17 |
| | | 10 | 0 |

In Vivo Activity of Anti-Myxovirus Compounds

In our experimental models for testing of anti-myxovirus activity, mice were intranasally infected with a mouse-adapted human influenza $A_2$ virus in an amount to cause development of acute influenza resulting in death of animals. When animals so infected were treated with Amantadine (the reference "positive control" substance) or representative Compounds A or B administered intraperitoneally, those compounds exhibited a significant antiviral effect against influenza virus infection.

The following experimental design was used:

ANIMALS:

Charles River, random bred white mice of female sex, 10–12 g starting weight. 20 mice per group.

VIRUS:

Mice were infected intranasally with influenza virus $A_2$/Aichi/2/68 in a dose indicated in the table.

COMPOUNDS:

Compounds were dissolved and subsequently diluted to their respective concentrations in phosphate buffered saline (PBS).

PROCEDURE:

Mice were weighed daily before inoculation and doses of the compounds adjusted according to the actual weight of the individual animal. Intraperitoneal administration of the compounds was done once a day for an aggregate of 16 days beginning one day before infection with the virus.

Clinical signs of disease and mortality were recorded daily. At the end of the experiment, survival rates and mean survival times of each group of animals were determined.

The results are shown in the following table:

| Exp. | Virus Dose ($LD_{50}$) | Group | Drug Dose (mg/kg/day) | Survival N** | % | Mean Survival Time* Days | Increase |
|---|---|---|---|---|---|---|---|
| 1 | 4.1 | Virus, only | 0 | 3/20 | 15 | 12.0 | 0 |
|   |     | AMAN | 75 | 11/20 | 55 | 14.1 | +1.9 |
|   |     | Compound A | 25 | 6/20 | 30 | 12.7 | +0.5 |
| 2 | 2.0 | Virus, only | 0 | 8/20 | 40 | 12.4 | 0 |
|   |     | AMAN | 75 | 16/20 | 80 | 15.3 | +2.9 |
|   |     | Compound B | 300 | 14/20 | 70 | 14.5 | +2.1 |
| 3 | 2.6 | Virus, only | 0 | 3/20 | 15 | 11.1 | 0 |
|   |     | AMAN | 75 | 16/20 | 80 | 15.1 | +4.0 |
|   |     | Compound B | 200 | 8/20 | 40 | 13.2 | +2.1 |
| 4 | 3.0 | Virus, only | 0 | 4/20 | 20 | 11.3 | 0 |
|   |     | AMAN | 75 | 15/19 | 79 | 15.0 | +3.7 |
|   |     | Compound B | 200 | 9/20 | 45 | 13.5 | +2.2 |

*Mean survival time (days) = number of mice alive each day (up to the last day of experiment) divided by total number of mice in group.
**Number of surviving animals divided by total number of animals infected.

Toxicity of Anti-Myxovirus Compounds in Mice

ANIMALS:

Charles River random bred white mice of female sex and 10–12 g of starting weight. 18 mice per group.

COMPOUNDS:

*IP route: 25-50-75-100-125-150200-300 mg/kg/day (Compound A); 25-50-100-150-200-300-400-500-600-700 mg/kg/day (Compound B);

**PO route: 50-100-200-300-400-500-750 mg/kg/day (Compound A); 200-300-400-500-750 mg/kg/day (Compound B).

*IP=intraperitoneal
**PO=oral

PROCEDURE:

Mice were weighed each day before administration of the compounds and doses adjusted according to the actual weight of individual animal.

The compounds were dissolved in and diluted to the proper concentrations with the isotonic phosphate-buffered saline (PBS). Administration of the compounds were done once a day for sixteen days every morning and the corresponding toxicities determined after 24 hours (acute) or on the seventeenth day of treatment (subacute).

EVALUATION:

All animals were observed for clinical signs of toxicity (weight loss, anorexia, ruffled fur, etc.) during the experiments. All dead or sacrificed animals were autopsied. Parameters evaluated were: the maximal non-toxic dose ($TD_o$), non-lethal dose ($LD_0$) and median toxic dose ($LD_{50}$). The following table shows the toxicity of representative Compounds A and B.

| Compound | Route of Administration | Acute $TD_0$ | Acute $LD_0$ | Acute $LD_{50}$ | Subacute $TD_0$ | Subacute $LD_0$ | Subacute $LD_{50}$ |
|---|---|---|---|---|---|---|---|
| A | IP | 25 | 75 | 160 | 25 | 75 | 125 |
|   | PO | 200 | >750 | >750 | 300 | >750 | >750 |
| B | IP | >750 | 450 | 550 | 400 | 450 | 500 |
|   | PO | >750 | >750 | >750 | 750[a] | >750 | >750 |

[a] Slight loss of weight.

As previously mentioned, when the compounds of the invention are used as antiviral agents they may be employed alone or in combination with the usual pharmaceutically acceptable carriers which are discussed in detail in U.S. Pat. Nos. 3,483,254, 3,496,220, 3,538,160, 3,534,084 and 3,592,934. The proportion of the antiviral agent with respect to the carrier is determined by its solubility and chosen route of administration.

The antiviral compounds of the invention can be administered according to the invention by any means that effects contact of the active ingredient compound with the site of influenza viral infection in the body of the living host. It will be understood that this includes the site prior to onset of infection as well as after the infection has established itself. For example, administration can be intranasally, orally, or parenterally, that is, subcutaneously, intravenously, intramuscularly, or intraperitoneally.

While the invention has now been described in terms of certain preferred embodiments, the skilled artisan will readily appreciate that various modifications, changes, omissions and substitutions may be made without departing from the spirit thereof. It is intended, therefore, that the present invention be limited solely by the scope of the following claims.

What is claimed is:

1. Endo-3-dimethylaminomethyl-endo-2-amino-1,2,3,4-tetrahydro-1,4-methanonaphthalene and its pharmaceutically acceptable acid addition salts.

2. The hydrochloride salt of the compound named in claim 1.

3. Endo-2-dimethylaminomethyl-1,2,3,4-tetrahydro-1,4-methanonaphthalene and its pharmaceutically acceptable acid addition salts.

4. The hydrochloride salt of the compound named in claim 3.

5. A composition of matter comprising an anti-viral effective amount of a compound selected from the group consisting of endo-3-dimethylaminomethyl-endo-2-amino-1,2,3,4-tetrahydro-1,4-methanonaphthalene, endo-2-dimethylaminomethyl-1,2,3,4-tetrahydro-1,4-methanonaphthalene and their pharmaceutically acceptable acid addition and a pharmaceutically acceptable carrier.

6. The composition of claim 5, wherein said carrier is selected from the group consisting of water, saline, aqueous dextrose and related sugar solutions and glycols.

7. The composition of claim 6, wherein said compound is present in amounts of from 0.5 to 25%, by weight.

8. A method for treating viral infections in a patient comprising administering to the patient an effective daily dose of a compound selected from the group consisting of endo-3-dimethylaminomethyl-endo-2-amino-1,2,3,4-methanonaphthalene, endo-2-dimethylaminomethyl-1,2,3,4-tetrahydro-1,4-methanonaphthalene and their pharmaceutically effective acid addition salts.

* * * * *